United States Patent [19]

Hochberger et al.

[11] Patent Number: 4,807,596
[45] Date of Patent: Feb. 28, 1989

[54] GUIDING PROBE

[75] Inventors: Jürgen Hochberger; Christian Ell, both of Erlangen, Fed. Rep. of Germany

[73] Assignee: Messerschmitt-Bölkow-Blohm GmbH, Munich, Fed. Rep. of Germany

[21] Appl. No.: 906,332

[22] Filed: Sep. 11, 1986

[30] Foreign Application Priority Data

Sep. 19, 1985 [DE] Fed. Rep. of Germany ....... 3533452

[51] Int. Cl.⁴ .............................................. A61B 1/00
[52] U.S. Cl. ..................................... 128/4; 128/303.1
[58] Field of Search ................ 128/3, 4, 5, 6, 7, 303.1, 128/303.13, 303.15, 395, 396, 397, 398

[56] References Cited

U.S. PATENT DOCUMENTS

| 2,424,064 | 7/1947 | Stegeman | 128/6 X |
| 4,146,019 | 3/1979 | Bass et al. | 128/6 |
| 4,211,229 | 7/1980 | Wurster | 128/303.1 |
| 4,233,493 | 11/1980 | Nath | 128/303.1 X |
| 4,273,535 | 6/1981 | Yamamoto et al. | 128/303.1 X |
| 4,503,854 | 3/1985 | Jako | 128/303.1 |
| 4,527,560 | 7/1985 | Masreliez | 128/303.1 |

Primary Examiner—William H. Grieb
Attorney, Agent, or Firm—Kenyon & Kenyon

[57] ABSTRACT

A guiding probe, in particular for an endoscope for surgical endoscopy with laser light, wherein the guiding probe comprises a flexible section which is resistant to high temperatures and substantially does not absorb the laser light used, and further including an auxiliary part for introducing the probe.

14 Claims, 4 Drawing Sheets

GUIDING PROBE

BACKGROUND OF THE INVENTION

In medicine, laser light is used, inter alia, for the controlled coagulation or vaporization of tissue, thereby removing it. Thus, a special advantage of laser light of a certain wavelength resides in its transferability by way of flexible light guides; this permits working with laser light under optical control with an endoscope even at sites in the human body difficult to reach otherwise. Thus, in many clinics laser endoscopy is already being used routinely in gastroenterology, urology, neurosurgery, pulmonology, etc. for the removal of benign and malignant tissue.

Now if, for example, in the region of the gastrointestinal tract a "tube-like" passage is constricted by the growth of a tumor or other causes, it can often be opened up again by means of laser light under endoscopic control. Here, advanced constrictions extending over a long distance (stenoses) present special difficulties.

For the upper digestive tract, several procedures are known:

If a stricture is endoscopically not passable, it is opened up by means of laser light in the forward direction. The natural course of the passage is often difficult to recognize especially in the case of extended malignant tumor stenoses due to irregular growth of the tumor, invading tissue neoformation along with crater-like tumor collapse, so that often a deviation from the natural passage course and opening of the wall by the laser beam occurs. According to specialists, the risk of perforation is as much as 30%.

A second method for the upper digestive tract consists in a combined laser and bougienage therapy, in which in case of endoscopic impassibility of a stricture the latter is first expanded by bougienage, the endoscope is guided through the stricture, and then the stenosis is "lasered open" by slowly retracting the endoscope from distal to proximal.

In many endoscopically reachable places, as for instance in the lower digestive tract, in the bronchial tract or in neurosurgery, however, bougienage is hardly possible—it is usually unpleasant and painful for the patient—and subject to a certain risk of perforation, and it usually requires several sessions on different days, thereby additionally lengthening the stay in the hospital.

SUMMARY OF THE INVENTION

The present invention is to avoid the disadvantages of the known devices; in particular a guiding probe is to be provided by means of which the endoscope can be guided with laser light in the canal also during the treatment.

The above and other objects of the present invention are achieved by a guiding probe, in particular for surgical endoscopy with laser light, wherein the guiding probe comprises in the region of the surgical treatment by laser light a portion flexible at least sectionwise, the melting or softening point of the portion being above the temperature rise caused by absorption of laser light.

First, the laserproof guiding probe according to the invention is introduced into the stricture, usually under endosopic control of radiological representation. If then the endoscopist, in proceeding with the endoscope and laser beam, orients himself by following the laserproof probe, he is sure to follow the natural passage course, resulting in a reduction of the risk of perforation.

Such a laserproof probe can be used, independently of the respective location, in principle at any point reachable with the laser beam, to offer a reliable orientation aid when opening a stricture by means of a laser beam.

BRIEF DESCRIPTION OF THE DRAWINGS

The invention will be described in greater detail in the following detailed description with reference to the drawings, in which.

DETAILED DESCRIPTION

Figure 1:
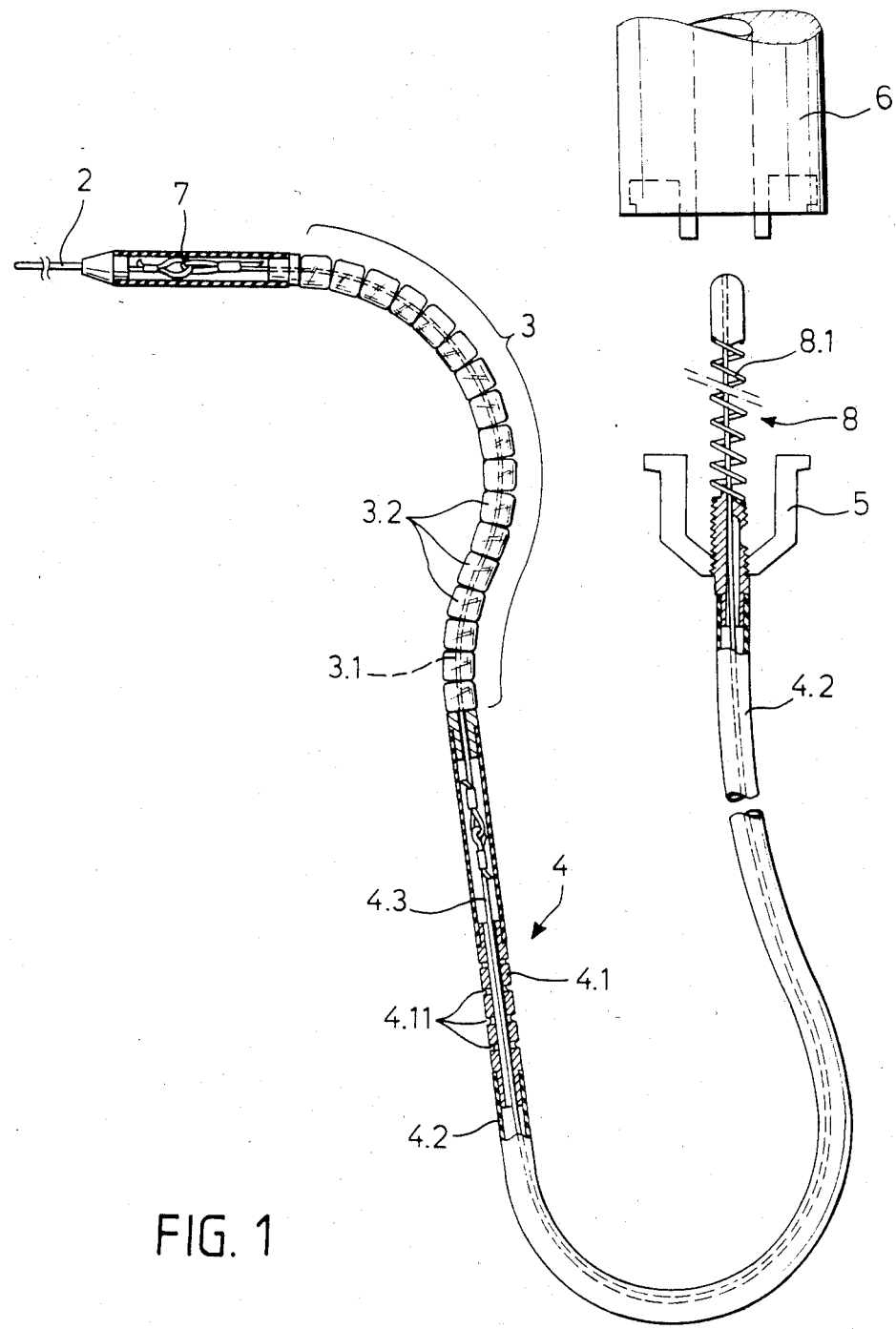
FIG. 1 shows a longitudinal section through a guiding probe.

With reference now to the drawings, the guiding probe 1 illustrated in FIG. 1 essentially comprises a flexible guiding tip 2, a flexible, laserproof section 3, and an extension part 4 with a coupling 5 for connection to a corresponding coupling piece 6 of a suction device. The guiding tip 2 comprises a comparatively thin, flexible, corrosion-resistant wire, which can be coupled selectively via a connection 7 to the laserproof section 3 and which is intended to facilitate thereby the introduction of the probe into a stricture, in that it serves as pathfinder for the generally less flexible section 3. This tip 2 is advantageously about 10 cm long.

The laserproof section 3 contiguous to the guiding tip 2 comprises a core wire 3.1, on which are strung cylindrical elements 3.2 in the manner of a string of beads. The elements 3.2 comprise a material resistant to high temperature, such as quartz glass or aluminum oxide ceramic, which has a melting point preferably above 1000° C. and which furthermore absorbs the laser light as little as possible. Chemically the material should, to the extent possible, be inert to the surrounding tissue and to the substances resulting when the tissue is burned by the laser light.

Figure 2:
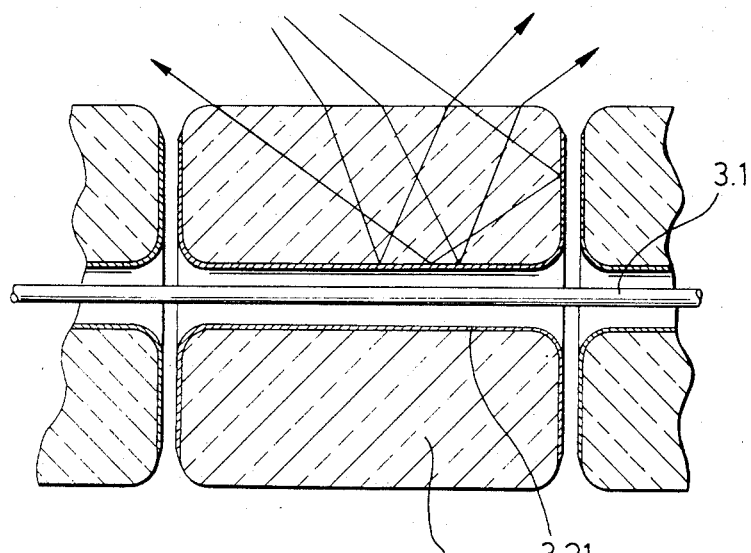
FIG. 2 shows a longitudinal section through the laserproof part of a guiding probe.

The core wire 3.1 itself should have similar properties as the elements 3.2, that is, a low absorption and high reflection capacity relative to the laser light, a high melting point, and chemical inertness. A tungsten wire of a diameter of 0.5 mm on which is applied by electroplating a high-purity gold film of about 30 microns using hard gold as an adhesion promoter has been found suitable for this purpose. Instead of tungsten, also a correspondingly gold-plated wire of a platinum-rhodium alloy (70/30) is suitable. For additional protection of the core wire 3.1 from the laser light, the cylindrical elements 3.2 may have at the end faces as well as at the walls of the inner bore a highly reflective layer 3.21, e.g., of vapor-deposited gold in a thickness of about 30 microns, as illustrated in FIG. 2. The laser light entering through the highly transparent elements 3.2 is reflected at these layers 3.21 and leaves the elements without getting to the core wire 3.1.

For an element 3.2 for endoscopic use of the guiding probe advantageous dimensions have been found to be an outside diameter of about 2.5 mm, an inner bore of 0.7 mm, and a length of about 5 mm. The entire section 3 has advantageously about 3 such elements 3.2.

The extension part 4 contiguous to section 3 comprises a drainage tube 4.1 provided with slits 4.11 and having the same diameter as section 3, to draw off the gases forming during the tissue erosion process, or to flush the treatment area. The drainage tube 4.1 opens into a flexible plastic hose 4.2, e.g. of Teflon, which carries at its end a coupling piece 5 for connection to a corresponding coupling piece 6 of a suction or flushing device not shown. The extension part 4 also comprises a central wire or cable 4.3, connected at one end with the core wire 3.1. The other end of wire 4.3 terminates in a tensioning device 8, which by means of a helical spring 8.1 exerts an adjustable pull. By this tensioning device the elements 3.2 are pushed together by means of the wire 4.3 and the core wire 3.1 and are slightly braced against each other. Thereby the section 3 is given a special flexible property, which permits, on the one hand, easy bending of section 3, while on the other hand exerting a light restoring force thereon.

Figure 3:
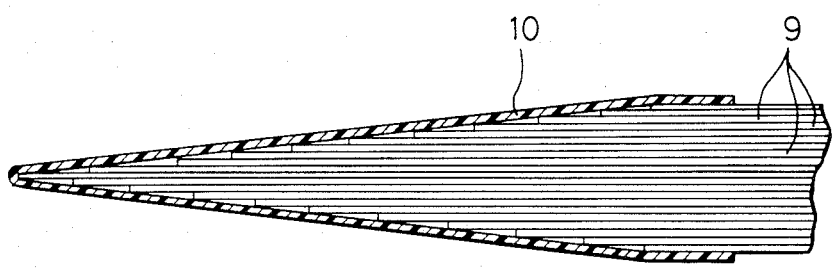
FIG. 3 shows a longitudinal section through a guiding probe of fiber material.

FIG. 3 shows another embodiment of a laserproof section of a guiding probe, which comprises a bundle of quarts glass fibers 9, the bundle tapering toward the tip. Fraying of the thus tapering fiber bundle is prevented by a conical ferrule 10, which is shrink-fitted on the fiber bundle or glued to it. The dimensions of the fiber bundle match those of the section 3 in FIG. 1; the extension part 4, not shown in FIG. 3 but shown in FIG. 1 is then fitted to the fiber bundle 9 shown in FIG. 3, except that here the central tensioning wire and the tensioning device can be dispensed with.

Figure 4:
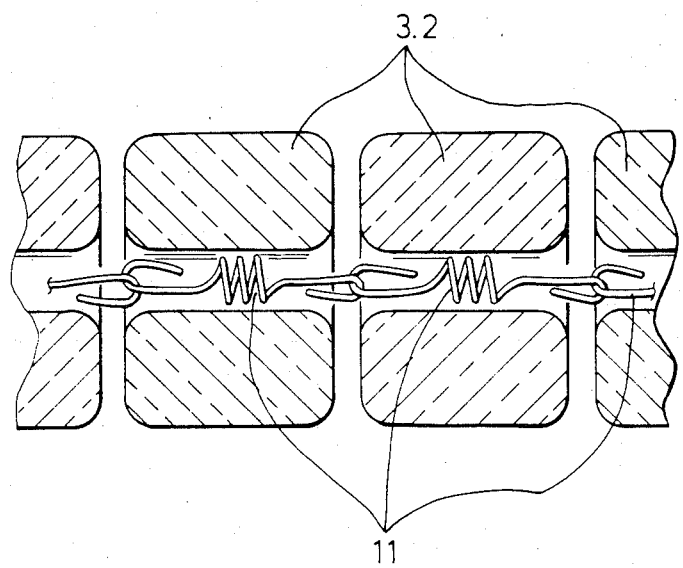
FIG. 4 shows a longitudinal section through the laserproof part of a guiding probe with elements strung together.
Figure 5A:
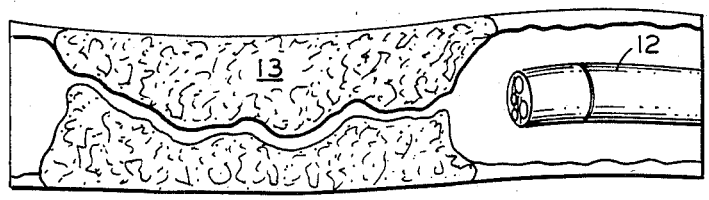
FIG. 5 (a–e) shows the use of a guiding probe for laser-endoscopic treatment of a stenosis.
Figure 5B:
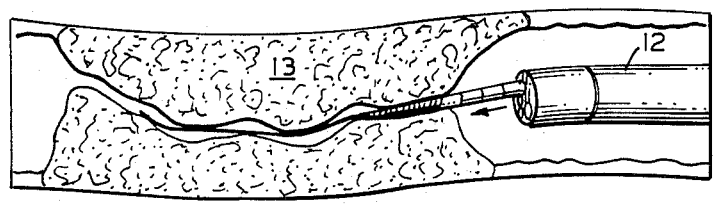
Figure 5C:
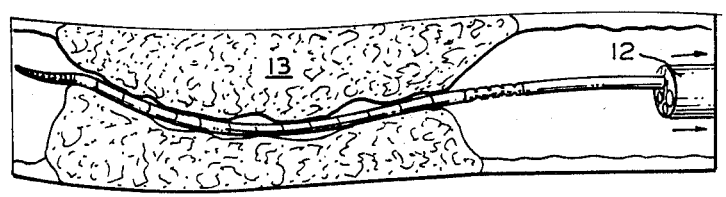
Figure 5D:
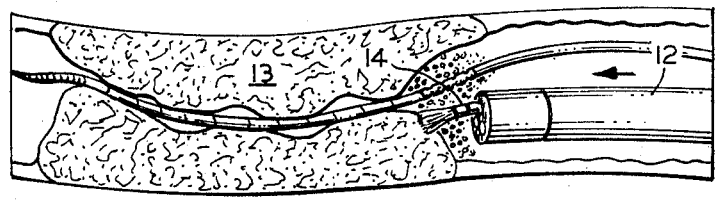
Figure 5E:
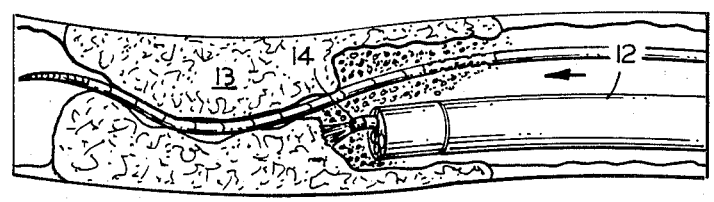

In FIG. 4 is shown an embodiment of a laserproof section of a guiding probe in which each cylindrical element 3.2 has a central, resilient connecting element 11, by means of which any number of elements 3.2 can be strung together or can be interchanged.

In FIG. 5, the use of a guiding probe according to the invention in the laserendoscopic elimination of a stenosis is described. First (FIG. 5a) a conventional endoscope 12 is brought to the beginning of a stenosis 13 of proliferating tissue. Then the guiding probe 1 of the invention is introduced through the biopsy canal of the endoscope 12 into the stenosis to be treated, under visual or radiological control (FIG. 5b). In so doing, the guiding probe is advanced far enough for the laserproof section 3 to be positioned in the stenosis 13, the drainage tube 4.1 being still exposed (FIG. 5c). As conventional endoscopes have only one biopsy canal, the endoscope 12 is retracted, the guiding probe remaining in the stenosis (FIG. 5c). The biopsy canal of the endoscope thus cleared is fitted with a light guide 14, which is connected with a laser light source, e.g., a neodymium YAG laser. The endoscope 12 thus equipped is moved again to the beginning of the stenosis 13 (FIG. 5d), whereupon then the operating surgeon can remove the stenosis around the guiding probe, without the guiding probe itself being damaged by the laser light (FIG. 5e).

In the foregoing specification, the invention has been described with reference to specific exemplary embodiments thereof. It will, however, be evident that various modifications and changes may be made thereunto without departing from the broader spirit and scope of the invention as set forth in the appended claims. The specification and drawings are, accordingly, to be regarded in an illustrative rather than in a restrictive sense.

We claim:

1. A guiding probe, for use in conjunction with an endoscope wherein the endoscope comprises a laser light guide transmitting laser light to an area of surgical treatment, and wherein the guiding probe allows a user of the endoscope to guide the laser light from the endoscope to the area of surgical treatment where the guiding probe is disposed, the guiding probe comprising an at least sectionwise flexible portion in the region of the surgical treatment, said portion having a melting or softening point which is above the temperature rise caused by absorption of laser light, said portion comprising a plurality of separate elements thereby minimizing the absorption of laser light.

2. The guiding probe recited in claim 1, wherein the portion comprises a plurality of elements comprising ceramic, glass or glass-ceramic, and further comprising a core wire, said plurality of elements being strung up on the core wire in the manner of a string of beads.

3. The guiding probe recited in claim 2, wherein the core wire comprises a precious metal or alloy.

4. The guiding probe recited in claim 2, wherein the core wire comprises at least one glass fiber.

5. The guiding probe recited in claim 2, wherein at least one of the core wire and the elements are provided at least partially with a layer for reflecting the laser light.

6. The guiding probe recited in claim 2, wherein the elements are cylindrical and have a coaxial bore.

7. The guiding probe recited in claim 1, wherein the portion comprises elements of ceramic, glass or glass-ceramic which include a central connecting element for stringing the elements together.

8. The guiding probe recited in claim 1, further comprising a flexible guiding tip thinner in diameter than the diameter of said portion.

9. The guiding probe recited in claim 2, wherein the elements are held together in an axial direction and clamped against each other by the core wire and spring means coupled to the core wire.

10. The guiding probe recited in claim 7, wherein the elements are held together by the connecting elements.

11. The guiding probe recited in claim 2, wherein the elements comprise at their frontal and end faces mutually overlapping collar pieces, such that they shield the core wire from the laser light even when the guiding probe is in a bent state.

12. The guiding probe recited in claim 1, wherein the portion is provided with a flexible extension part for direct introduction or indirect introduction via an endoscope canal.

13. The guiding probe recited in claim 12, wherein the extension part comprises one of a tubular or hose type line with openings for the removal by suction of materials or for flushing.

14. The guiding probe recited in claim 1, wherein the portion comprises a fiber bundle, the elements of said portion comprising fibers of said fiber bundle of glass, ceramic or glass-ceramic.

* * * * *

UNITED STATES PATENT AND TRADEMARK OFFICE
CERTIFICATE OF CORRECTION

PATENT NO. : 4,807,596
DATED : February 28, 1989
INVENTOR(S) : J. Hochberger et al It is certified that error appears in the above-identified patent and that said Letters Patent is hereby corrected as shown below:

In Column 1, line 66, change "...endosopic control of ..."
    to read --...endoscopic control or ...--

In Column 3, line 5, change "...about 3 such..."
    to read --...about 30 such ...--

Signed and Sealed this

Thirty-first Day of October, 1989

Attest:

DONALD J. QUIGG

Attesting Officer   Commissioner of Patents and Trademarks